US010398412B2

(12) United States Patent
Ben-Lavi et al.

(10) Patent No.: US 10,398,412 B2
(45) Date of Patent: Sep. 3, 2019

(54) 3D ULTRASOUND IMAGE STITCHING

(71) Applicants: CENTRE FOR IMAGING TECHNOLOGY COMMERCIALIZATION, London (CA); THE UNIVERSITY OF WESTERN ONTARIO, London (CA)

(72) Inventors: Eliezer Azi Ben-Lavi, London (CA); Aaron Fenster, London (CA)

(73) Assignees: Aaron Fenster, London, Ontario (CA); CENTRE FOR IMAGING TECHNOLOGY COMMERCIALIZATION, London, Ontario (CA)

( * ) Notice: Subject to any disclaimer, the term of this patent is extended or adjusted under 35 U.S.C. 154(b) by 109 days.

(21) Appl. No.: 15/562,999

(22) PCT Filed: Mar. 31, 2015

(86) PCT No.: PCT/CA2015/000210
§ 371 (c)(1),
(2) Date: Sep. 29, 2017

(87) PCT Pub. No.: WO2016/154714
PCT Pub. Date: Oct. 6, 2016

(65) Prior Publication Data
US 2018/0049721 A1   Feb. 22, 2018

(51) Int. Cl.
*A61B 8/08* (2006.01)
*A61B 8/00* (2006.01)
(Continued)

(52) U.S. Cl.
CPC .......... *A61B 8/5253* (2013.01); *A61B 8/0891* (2013.01); *A61B 8/4477* (2013.01);
(Continued)

(58) Field of Classification Search
CPC combination set(s) only.
See application file for complete search history.

(56) References Cited

U.S. PATENT DOCUMENTS 6,728,424 B1 * 4/2004 Zhu ....................... G06T 3/0068
382/128
8,684,932 B2 * 4/2014 Kataguchi ................ A61B 8/06
600/441

(Continued)

*Primary Examiner* — Anand P Bhatnagar
(74) *Attorney, Agent, or Firm* — Brunet & Co. Ltd.

(57) ABSTRACT

A computer-implemented method for combining two 3-dimensional ultrasound images of a patient's body part containing blood vessels into a single 3-dimensional ultrasound image of that body part with a greater field of view. Blood vessels within the body part are used for registration. The two ultrasound images are preprocessed using a vessel enhancement algorithm to derive two corresponding enhanced images. The enhanced images can undergo a registration process based upon minimizing a mean-square-difference metric to derive an enhanced rigid transform, which represents a transform that maps the first enhanced image onto the second enhanced image. The two enhanced images are seamlessly combined via a blending process (via the use of a distance transform based weighting of the voxel values) to derive an output image.

11 Claims, 7 Drawing Sheets

(51) Int. Cl.
  *G06T 3/40* (2006.01)
  *G06T 7/32* (2017.01)
  *G06T 7/12* (2017.01)

(52) U.S. Cl.
  CPC ............ *A61B 8/483* (2013.01); *A61B 8/5223* (2013.01); *G06T 3/4038* (2013.01); *G06T 7/12* (2017.01); *G06T 7/32* (2017.01); *G06T 2207/10136* (2013.01); *G06T 2207/20016* (2013.01); *G06T 2207/20048* (2013.01); *G06T 2207/20076* (2013.01); *G06T 2207/20221* (2013.01); *G06T 2207/30101* (2013.01)

(56) References Cited

U.S. PATENT DOCUMENTS

| | | | |
|---|---|---|---|
| 9,216,065 B2* | 12/2015 | Cohen | A61B 5/0044 |
| 2007/0083114 A1* | 4/2007 | Yang | A61B 8/00 600/437 |
| 2008/0009727 A1* | 1/2008 | Kataguchi | A61B 8/06 600/437 |
| 2008/0247622 A1* | 10/2008 | Aylward | A61B 90/36 382/131 |
| 2011/0299753 A1* | 12/2011 | Suri | A61B 8/0858 382/131 |
| 2011/0299754 A1* | 12/2011 | Suri | G06T 7/0012 382/131 |
| 2013/0028493 A1* | 1/2013 | Rangwala | G06T 7/0012 382/128 |
| 2014/0369583 A1* | 12/2014 | Toji | A61B 8/06 382/131 |
| 2015/0327805 A1* | 11/2015 | Ben-Haim | A61B 6/037 600/411 |
| 2016/0030007 A1* | 2/2016 | Tsujita | G06T 15/08 600/438 |
| 2018/0082433 A1* | 3/2018 | Ben-Lavi | G06T 5/20 |

* cited by examiner

3D ULTRASOUND IMAGE STITCHING

CROSS-REFERENCE TO RELATED APPLICATIONS

This application is a § 371 national phase of International Application No. PCT/CA2015/000210, filed on Mar. 31, 2015, which application is incorporated by reference herein.

FIELD OF THE INVENTION

The present invention relates generally to the field of ultrasound processing methods, and more particularly to methods for stitching two 3D ultrasound images into a single image with a greater field of view.

BACKGROUND OF THE INVENTION

The use of ultrasound imaging methods have become increasingly popular in medical diagnosis because it is non-invasive, easy to use, and does not generally subject patients to the risks associated with electromagnetic radiation. In typical conventional ultrasound systems, sound waves of very high frequency (around 2 MHz to 10 MHz) are transmitted into a patient, and the echoes reflected from structures inside the patient's body are processed to derive and display information relating to such structures.

The 3-dimensional ultrasound ("3DUS") image of a body part that is captured by a probe may cover a certain area/volume; in some instances, it may be desirable to be able to obtain a 3DUS image that covers a larger area with the same detail. Therefore, there is an advantage in providing a technique by means of which two 3DUS images of a patient's body part may be combined or stitched together into a single 3DUS image having a greater field of view.

SUMMARY OF THE INVENTION

Disclosed herein is a computer-implemented method for combining two 3D ultrasound images of patient's body part having blood vessels into a single 3D ultrasound image with a greater field of view. One or more blood vessels within the body part may be used for image registration purposes.

In accordance with one aspect of the invention, a computer-implemented method is provided for combining two 3D ultrasound images of a body part containing at least one blood vessel, into a single 3D ultrasound image with a greater field of view, comprising: using at least one processing unit to receive (i) a first 3D ultrasound image of said body part, (ii) a second 3D ultrasound image of said body part, and (iii) an initial transform, wherein the first ultrasound image overlaps with the second ultrasound image in an overlapping region; using the at least one processing unit to perform a preprocessing vessel enhancement step on the first 3D ultrasound image in order to derive a first enhanced image; using the at least one processing unit to perform a preprocessing vessel enhancement step on the second 3D ultrasound image in order to derive a second enhanced image; using the at least one processing unit to perform a registration step on the first enhanced image, the second enhanced image and the initial transform, in order to derive a refined transform; using the at least one processing unit to perform a blending step on the first and second enhanced images, using the refined transform, by application of a distance transform based weighting of the voxel values in the overlapping region of the first and second enhanced images, thereby obtaining an output image; and using the at least one processing unit to output the output image.

DESCRIPTION OF THE DRAWINGS

The novel features which are believed to be characteristic of the method according to the present invention, as to their organization, use, and method of operation, together with further objectives and advantages thereof, may be better understood from the following drawings in which presently preferred applications of the invention may be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Figure 1:
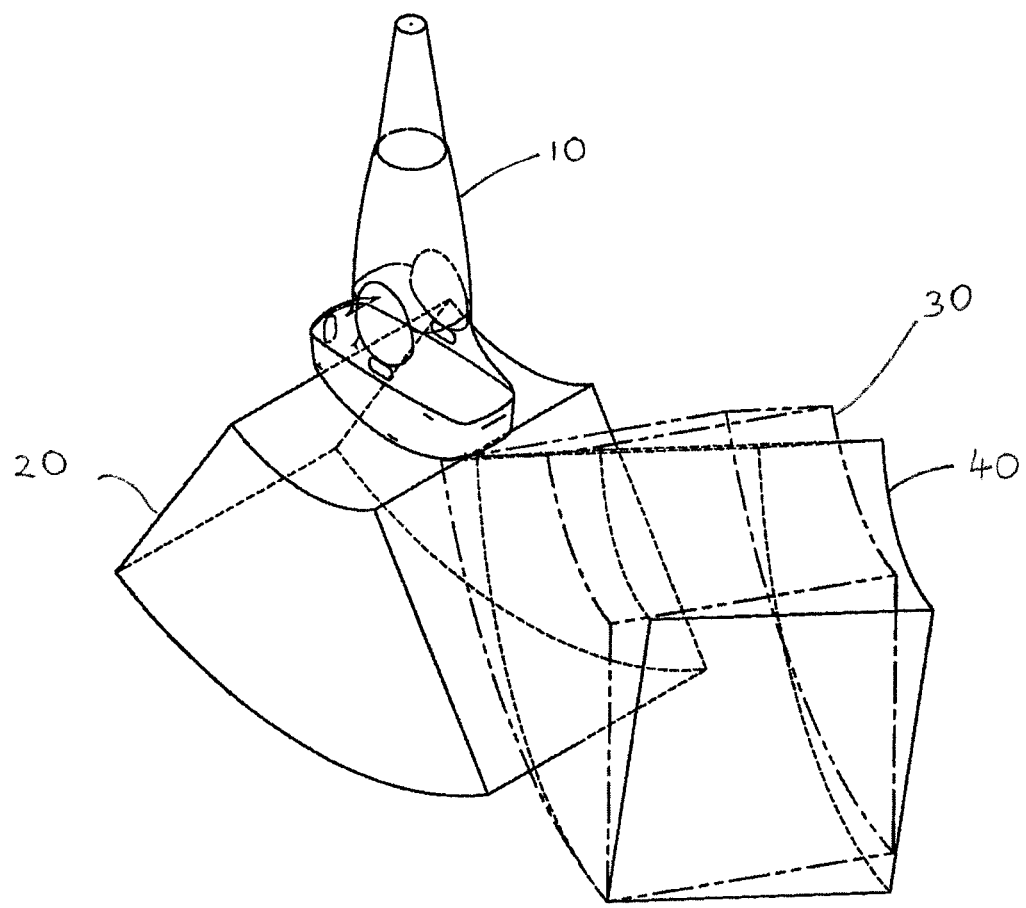
FIG. 1 is a schematic representation of a registration process as applied to 3D ultrasound images.

The description that follows, and the embodiments described therein, is provided by way of illustration of an example, or examples, of particular embodiments of the principles of the present invention. These examples are provided for the purposes of explanation, and not of limitation, of those principles and of the invention. In the description, like parts are marked throughout the specification and the drawings with the same respective reference numerals. The drawings are not necessarily to scale and in some instances proportions may have been exaggerated in order to more clearly depict certain embodiments and features of the invention.

In this disclosure, a number of terms and abbreviations are used. As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

In order that the invention may be more fully understood, it will now be described, by way of example, with reference to the accompanying drawings in which FIG. 1 through FIG. 7 illustrate aspects of the present invention.

Disclosed herein is a method to combine two 3DUS images of a patient's body part into a single 3DUS image of that body part with a greater field of view. The present invention is described particularly in the context of an application for 3DUS imaging of a portion of a patient's liver. However, it should be understood that the method discussed herein may be applied to practically any body part, organ or tissue which contains blood vessels. The output image will contain the volume which is included exclusively in either one of the two images and not the other. It will also contain the volume which is included in both images, meaning the volume in which the images overlap. In the former volume, the value of the output image will be identical to the interpolated value of the one image which includes this volume (and by definition there is only one such volume) and in the latter volume, the value of the output image will be determined by blending the interpolated values of both input volumes (by definition these volumes appears in two images so both image values need to be taken into consideration). A blending formula will be applied which creates a seamless output image, meaning that the transition from volume that exclusively belongs to either one of the input images to the overlap volume is smooth and natural. The overlap area will contain a weighted averaging of the interpolated values from both images.

A prerequisite to the generation of the output image is knowledge of the relative poses of the original images in the physical coordinate system, which is patient aligned—for example, Left Posterior Superior (LPS) which is the coordinate system defined in the Digital Imaging and Communications in Medicine ("DICOM") standard. In other words, the rigid body transform between the two images needs to be known. Often this transformation can be approximated by tracking the pose of the ultrasound probe using a stereoscopic camera or an electromagnetic tracking device. Alternatively, it could be produced by a human user by manually selecting corresponding landmarks in both images, followed by calculation of a transform by the well-known Procrustes algorithm. However, relying on these sources of information introduces errors which stem from patient motion in the period between when the two images are acquired in the first cases and from errors in selecting the corresponding landmarks in the second case. The effect of the transformation error can degrade the final image because if the images are not accurately aligned, the output image will have blurring artifacts in it. Therefore to produce a valuable image, it is desirable to reduce the transformation error to as low as possible and this may be achieved through the use of an image registration method.

Figure 2:
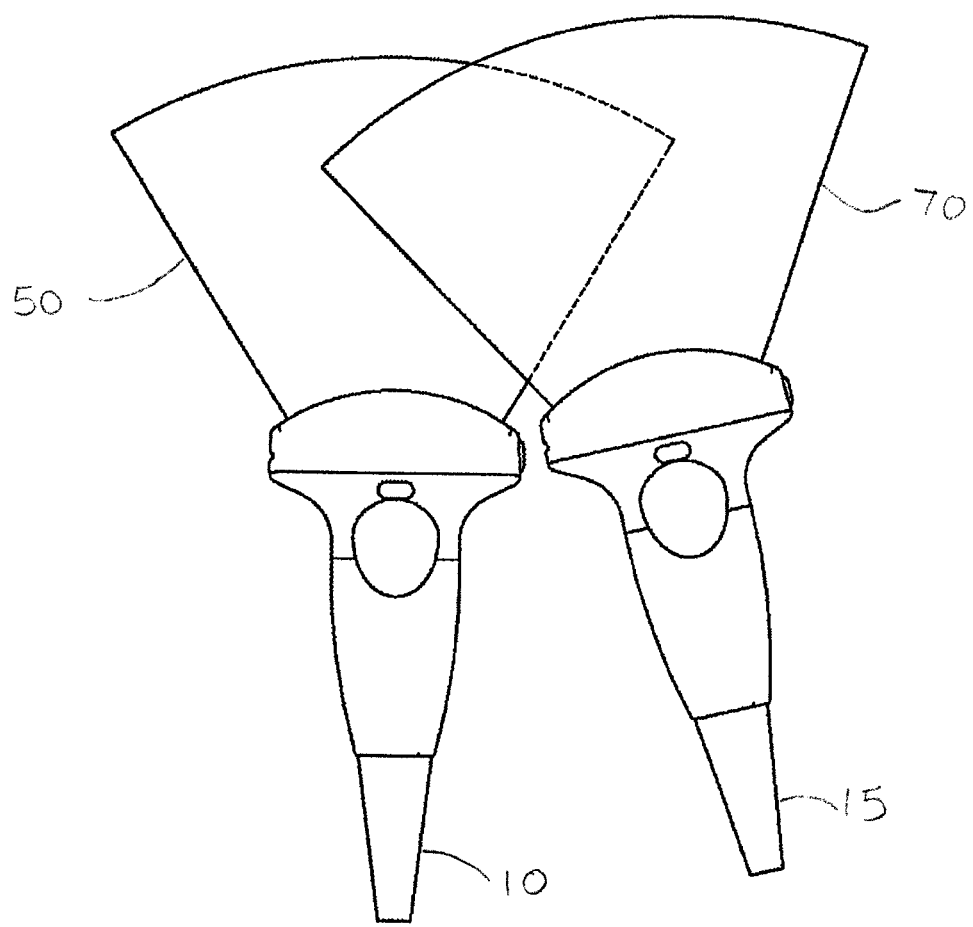
FIG. 2 illustrates a cross section view of the stitched image generated from two partially overlapping 3DUS images.

FIG. 1 is a schematic representation of the registration process. The fixed image that is detected by a probe 10 is represented by volume 20. The initial position of a moving image is depicted by the dashed wireframe volume of 30. The moving image after registration is depicted by the solid wireframe volume of 40. The position of the moving image is slightly adjusted by the registration process and this produces a more accurate final image. FIG. 2 is a cross section view depicting a stitched image that is generated from two overlapping 3DUS images (as detected by probes 10 and 15).

Figure 3:
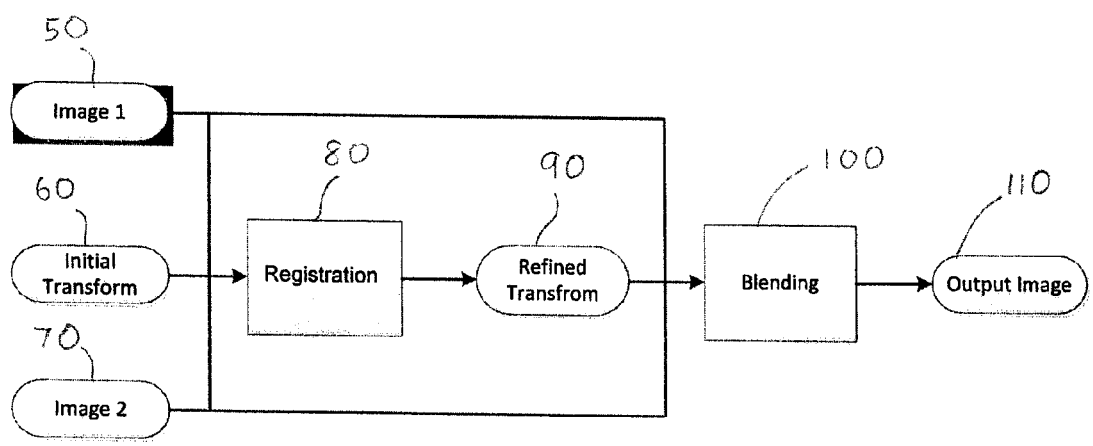
FIG. 3 is a block diagram illustrating the overall process for the stitching pipeline for two 3D ultrasound images.

Referring to FIG. 3, this is a block diagram illustrating the overall pipeline of the present method. The disclosed method is implemented by a computer provided with at least one processor or processing unit, a memory or storing unit and communications means for receiving and/or transmitting data. The computer may also include or be connected to a display unit for displaying the output image. Instructions are stored on the memory, and upon execution of the instructions, the processor performs the steps of the method. The disclosed method may also be embodied as a computer readable memory having recorded thereon, instructions that, upon execution by a processing unit, perform the described steps. The disclosed method has three inputs and one output. The inputs are two 3DUS images (50 & 70) showing the part of the patient's body that is being analyzed (for example, a portion of the liver) and an initial rigid transform 60 which registers the two images (50 & 70). The output from the registration step (step 80) is a refined rigid transform 90. The initial rigid transform 60 is only required to be sufficiently close to the true value; however, some degree of error is allowed. A person skilled in the art would be able to determine a suitable initial rigid transform; simply as an example, the initial transform could be chosen to be one which is say translated a distance of 1 cm, and is rotated an angle of less than 20° from the fixed image. The registration algorithm 80 will try to refine the input initial transform 60 and reduce the registration error, thus improving the alignment of the images compared to the initial transform 60. After the transform between the images has been established by the registration process (step 80), the input images then undergo a blending process (step 100), which generates a combined output image 110.

Registration.

The most common method for registration is to find a transform which minimizes a cost function or a metric which measures how similar the images are under a given transform. To obtain the value of the cost function, the speculated transform is applied to one of the images, which is commonly termed the "moving image", so that is resampled to the coordinate system of the other image, which is commonly termed the "fixed image". The cost function is calculated by simultaneously traversing the fixed image and the transformed moving image and applying some function of the intensity difference of the corresponding voxels. The function will quantify how similar the two images are; for images that are similar, the function will give a low value and for images which are different, the function will give a high value. The assumption is that if the transform is correct then the underlying images will be similar; on the other hand any error in the transform will make the images less similar and hence the value of the cost function will increase. For illustration purposes, consider the case where the images are identical yet one image is translated with respect to the other. In such a case, from the standpoint of the cost function, they will not be identical since as one traverses the images voxel by voxel, the difference in intensities will be measured due to the shifted voxels. The moving image needs to be translated correctly by the registration algorithm and then the cost function will obtain its minimal value. Thus, a transform which minimizes the cost function has a better chance of being the transform which correctly maps the image on to the other. Finally, quantifying the dissimilarity between images under a given transform enables the usage of numerical optimization methods, such as gradient descent, to find the transform which minimizes the cost function. For this, the rigid body transform is parameterized by 6 variables—3 to account for rotation and 3 for translation—and this defines the search space for the optimization procedure. The optimization starts from a position in this six dimensional space which is given by the parameterization of the initial transform which was mentioned earlier. The optimization procedure makes incremental changes to the current transform striving to minimize the value of the cost function. Eventually the changes become small, which is what happens at local minima, and this means that the optimization converged to a solution. This solution is the refined transform 90 discussed earlier. There are a few metrics which are widely accepted for image registration. One common metric is the simple Mean Square Difference metric, which simply subtracts the two images and takes the average squared difference of intensities. For identical images, the value of this metric is 0 which is the absolute minimum it can be. Other metrics are the Normalized Cross Correlation ("NCC"), which allows for linear transformation of intensities between images to account for different gain level and Mutual Information ("MI"), which can be used for registering images from different modalities (e.g. Computer Tomography ("CT") image to Magnetic Resonance ("MR") image).

The registration techniques mentioned above are usually applied to original images themselves. Some methods do apply some preprocessing to remove, for example by applying a Gaussian kernel, median filtering or Anisotropic Diffusion. However, these methods do not fundamentally change the images, they merely clean the noise. When applying NCC and MI methods, it is understood that while such methods worked fine in some cases, in many cases the transform returned was not accurate resulting in a poor quality of the blended images due to blurring artifacts. The reason for the deficient performance of standard methods on 3DUS images could be attributed to two facts: the first being the presence of image speckle in ultrasound compared to other modalities like CT or MRI. The second is that the angle of incidence of the ultrasonic wave has an effect on the image. So assuming a rotation of the probe between two images, the images will not only be rotated with respect to each other but they will also appear different.

Figure 4:
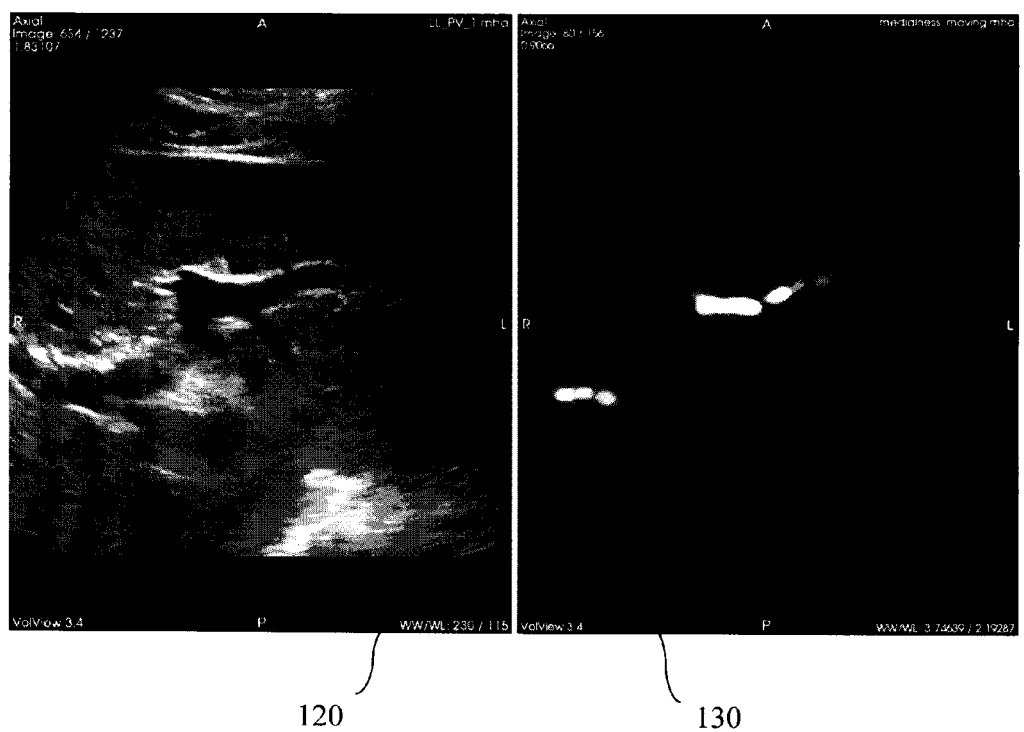
FIG. 4 is an example illustrating the effects of vessel enhancement on a 3D ultrasound image.
Figure 5:
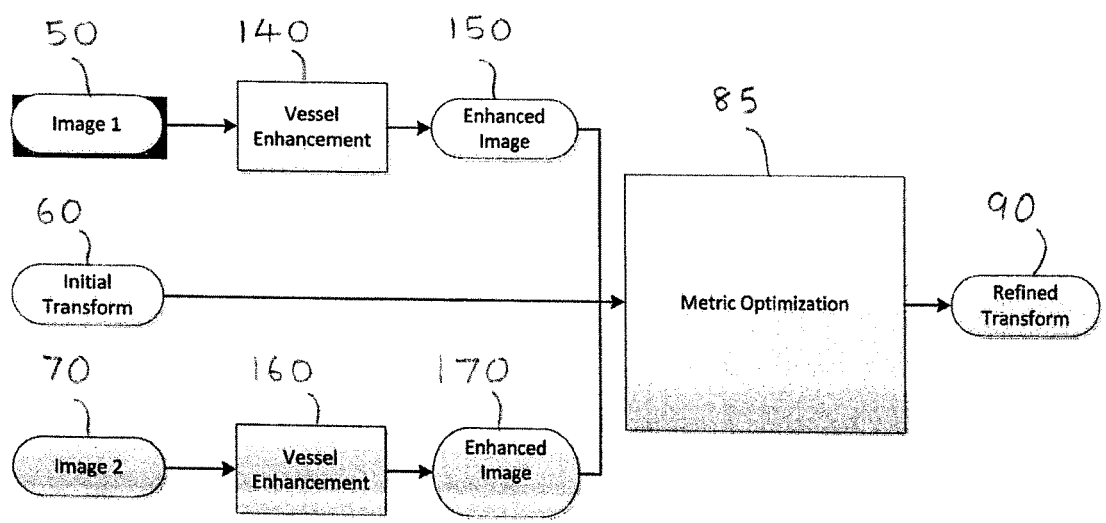
FIG. 5 is a block diagram showing the registration process.

To resolve this issue, it is contemplated that blood vessels (which are abundant in the liver) may be used for registration. A preprocessing algorithm is applied to each of the two 3DUS images in order to enhance blood vessels and suppress all other structures. In the resulting enhanced images, a voxel on a vessel will have a high intensity and other voxels will have lower intensities. This process eliminates much of the noise in the images and enhances the distinct features in the image, i.e. the blood vessels, while suppressing other features. An example illustrating the result of vessel enhancement is shown in FIG. 4. The view on the left hand side 120 is the original 3DUS image. The image on the right hand side 130 is the corresponding enhanced image. It can be seen in the enhanced image that the vessel areas are bright, whereas other areas are dark.

After such preprocessing, the enhanced images are registered by minimizing the Means Square Difference metric. This metric is applicable here because in both images, the intensity value corresponds to vessel probability and under correct transform, vessels in the fixed image will map to their counterparts in the moving image and thus the difference in intensity probability of corresponding voxels will be minimized. An illustration of the algorithm pipeline is presented in FIG. 5.

Vessel Enhancement.

The preprocessing stage requires producing accurate 3DUS output images. Accuracy is measured by two factors: the first is specificity, which means that if a voxel has a relatively high value in the output image it is in fact on a vessel; the second is sensitivity, which means that if a voxel is on a vessel it will have a relatively high value in the output image. The filter need not be fully accurate but we strive to make it is accurate as possible since filter accuracy is critical to getting a good registration.

There are many published vessel enhancement and segmentation methods. (A comprehensive review is provided by Lesage, David et al. "A review of 3D vessel lumen segmentation techniques: Models, features and extraction schemes." *Medical image analysis* 13.6 (2009): 819-845). Although there are many methods that have been successfully applied to CT and MR images, finding a method that will work well for 3DUS images is more challenging, since there are far fewer publications directed to 3DUS vessel segmentation than there are directed to other modalities. Several methods for 3DUS vessel enhancement were attempted, including the popular Frangi method (See Frangi, Alejandro F. et al. "Multiscale vessel enhancement filtering." *Medical Image Computing and Computer-Assisted Intervention—MICCAI'98*. Springer Berlin Heidelberg, 1998. 130-137), but the performance on the 3DUS images was problematic, judging by the above criteria of specificity and sensitivity. One approach that was found to be particularly promising is based on publications by Pock (see Pock, Thomas et al. "Multiscale medialness for robust segmentation of 3d tubular structures." *Proceedings of the Computer Vision Winter Workshop*. Vol. 2005. 2005), and by Krissian (see Krissian, K. et al. "Multiscale segmentation of the aorta in 3D ultrasound images." *Engineering in Medicine and Biology Society*, 2003. *Proceedings of the 25th Annual International Conference of the IEEE*. Vol. 1. IEEE, 2003) who used it for segmenting the aorta in 3DUS.

In Krissian (see Krissian, Karl et al. "Model-based detection of tubular structures in 3D images." *Computer vision and image understanding* 80.2 (2000): 130-171), the vessel is modeled as a cylindrical object and the intensity of the image at the cross section is modeled as a circular Gaussian blob. From this theoretical model, a filter is derived that is optimal for detecting objects whose intensity at the cross section is a Gaussian blob. The relationship between the radius of the vessel and the scale in which it is best detected is studied. Thus, by varying the scale, it is possible to detect vessels with a range of radii, which makes the method a multi-scale one. This property is useful in the present circumstances since it is desirable to be able to enhance vessels that are between 2 to 7 mm in radius. The method taught by Krissian involves first estimating the cross sectional plane of the vessel and then applying a response function which analyzes the gradient information in that plane. More details regarding the filter are discussed below. It should be noted that it was empirically found that resampling the input image to 1 mm isotropic spacing prior to applying the disclosed method, greatly reduces the computation time without a noticeable impact on the results.

Orientation Calculation.

A popular way to calculate the local orientation of a tubular object which was used by Frangi (see Frangi, Alejandro F. et al. "Multiscale vessel enhancement filtering." *Medical Image Computing and Computer Assisted Intervention—MICCAI'98*. Springer Berlin Heidelberg, 1998. 130-137) and Sato (see Sato, Yoshinobu et al. "Three-dimensional multi-scale line filter for segmentation and visualization of curvilinear structures in medical images." *Medical image analysis* 2.2 (1998): 143-168), among others, is to compute an Eigen decomposition of the Hessian matrix, which is the matrix of second derivatives of the image. This approach is based on treating the vessel as an intensity ridge or valley of the image and estimating the direction of the ridge or valley. Using a second degree Taylor expansion of the image intensity it can be shown that this direction corresponds to the eigenvector with the smallest eigenvalue of the Hessian matrix. Based on the eigenvalues of the Hessian metric, Frangi and Sato design a response function that enhances tubular structures; this approach is often used as a preprocessing method, which is followed by a full vessel segmentation.

Another method is based on the analysis of image gradient directions in the neighborhood of the voxel. It is noted that for vessels, the gradient magnitude will be strongest at the walls of the vessel compared to the inside of the vessel and a small neighborhood outside the vessel. Moreover, the gradient vectors will point outwards from the centerline because the vessel is darker than surrounding tissue in 3DUS. It follows therefore, that if a voxel lies on the centerline, the strongest gradients in its neighborhood will be roughly perpendicular to the tangent of the centerline. Thus, to find the vessel orientation we need to find a direction vector which minimizes the average projection of the gradients in the neighborhood of the vessel. It can be shown that this direction can be calculated by Eigen decomposition of the local structure tensor matrix which is the covariance of the gradient vectors in the neighborhood of the voxel. It was decided to use the structure tensor over the Hessian, since the former involves only first derivatives while the latter involves use of second derivatives, which could be detrimental when applied to the noisy 3DUS data.

Let I be an Image which is a function $\mathbb{R}^3 \to \mathbb{R}$. Let $G_\sigma$ be a multivariate Gaussian kernel with standard deviation $\sigma$ and let $\nabla_\sigma I$ be the gradient of image I obtained by the convolution with the derivatives of kernel $G_\sigma$ and multiplied by $\sigma$ for scale space normalization. The local structure tensor of an image is defined as the outer product of the gradient smoothed by a second Gaussian:

$$T_{\sigma_1,\sigma_2} = G_{\sigma_2} * (\nabla_{\sigma_1} I \cdot \nabla_{\sigma_1} I^t) \quad (1)$$

Krissian teaches, based on assumptions of the vessel's intensity profile model, that for maximum response for a vessel with radius r, the values $\sigma_1$ and $\sigma_2$ should be set according to:

$$\sigma_1 = \frac{r}{\sqrt{2}} \quad \sigma_2 = \frac{r}{2\sqrt{2}} \quad (2)$$

Figure 6:
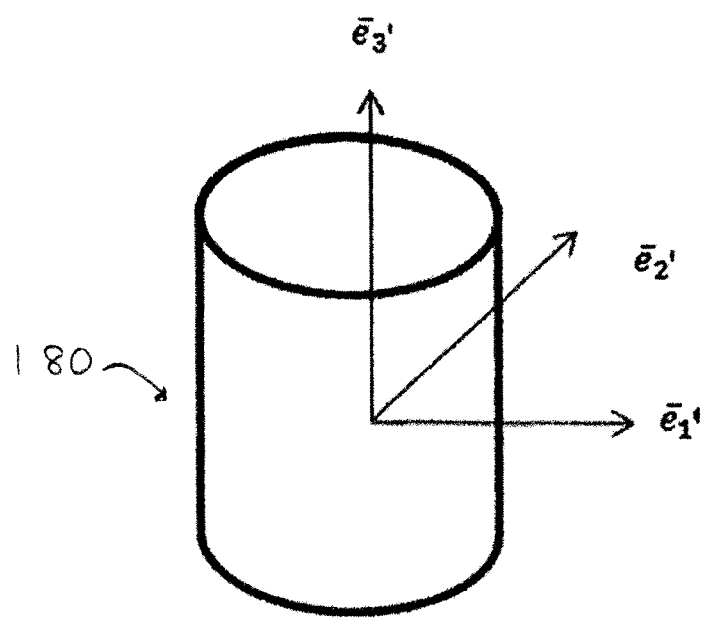
FIG. 6 illustrates the calculation of local orientation.

$T_{\sigma_1,\sigma_2}$ is a matrix at each voxel of the image. Denote $\mu_1 \geq \mu_2 \geq \mu_3 \geq 0$ as eigenvalues of $T_{\sigma_1,\sigma_2}$ and $e_1$, $e_2$, $e_3$ are the corresponding eigenvectors normalized to unit magnitude. These are depicted in FIG. 6, where the cylinder models a vessel, and $e_1$, $e_2$, $e_3$ are the eigenvectors of the structure tensor matrix. $e_3$ gives the best fit estimate of direction perpendicular to the strongest gradients in the neighborhood of the voxel. Thus, $e_3$ corresponds to the estimate of the centerline tangent's direction and $e_1$, $e_2$, which are orthogonal to it, span the cross sectional plane. Once the direction is obtained, a function which looks at the cross-sectional plane is designed such that it gives high response for tubular objects.

Response Function.

The estimate of the centerline tangent direction also yields an estimate of the cross section of the vessel. The filter enhances vessels with specific radius so the former provides the estimated location of the circumference of the vessel in the plane. If the inspected voxel is indeed on the centerline of the vessel with the corresponding radius, then it is expected to have the vessel walls at the estimated circumference. The response function analyzes the image gradients at the estimated circumference and gives a numerical value which corresponds to how well they fit the vessel cross section model. The response function has three terms which look at different aspects of the distribution of the gradients and are multiplicatively combined together to yield the final response.

In the first term, the sum of the gradient projection on the radial direction across the estimated circumference is considered. As mentioned earlier, it is expected that there would be strong gradient responses along the circumference at the vessel walls. On top of that, all the gradients' projection on the radial vector along the circumference should be positive since in 3DUS the vessel appears darker than the surrounding tissue. A negative sum of projection stands in contradiction to the vessel appearance model and therefore indicates that the inspected voxel does not lie on a vessel. A low sum of projections reduces the probability that a vessel is present because it can happen in two cases: either the absolute of the gradient along the circumference is low, which stands in contradiction to the requirement for strong gradients along the vessel walls, or there are both negative and positive projection terms which cancel each other out, which contradicts the requirement of positive gradient along the circumference of the vessel.

Mathematically, let us define the integral:

$$B_\sigma(x) = \frac{1}{2\pi\tau\sigma} \int_{\alpha=0}^{2\pi} \nabla_\sigma I(x + \tau\sigma v_\alpha) \cdot v_\alpha d\alpha \quad (3)$$

Where:

$$v_\alpha = e_1 \cos\alpha + e_2 \sin\alpha \; \alpha \in [0, 2\pi] \quad (4)$$

and x is the 3D coordinate of the voxel in the image. This expression integrates the gradient in the direction towards x over a circle centered at x whose radius is $\tau\sigma$. Here we also have $\sigma = \sigma_1$. According to Krissian, the optimal value for $\tau$ is $\sqrt{3}$. In practice the expression for $B_\sigma(x)$ is calculated using summation instead of integration:

$$B_\sigma(x) = \frac{1}{N} \sum_{i=1}^{N} \nabla_\sigma I(x + \tau\sigma v_{\alpha_i}) \cdot v_{\alpha_i} \quad (5)$$

Where $$\alpha_i = \frac{2\pi}{N}$$

i and N is the number of radial samples used (e.g. N=20).

$B_\sigma(x) < 0$ indicates that the structure is unlikely a vessel. Therefore, we define the first term of the response function as:

$$B_\sigma^+(x) = \begin{cases} 0, & B_\sigma(x) < 0 \\ B_\sigma(x), & B_\sigma(x) \geq 0 \end{cases} \quad (6)$$

The second term of the response function measures the variability of the radial gradient magnitude along the circumference of the vessel. The vessel is assumed to be radially symmetric and therefore the radial intensity gradient should be fairly constant along its circumference. A high variance means big differences in gradient magnitude in different part of the circumference which lowers the probability of the central voxel being on the centerline. Mathematically, we denote the individual terms which constitute the summation in (5):

$$b_i(\alpha_i) = \nabla_\sigma I(x + \rho\sigma v_{\alpha_i}) \cdot v_{\alpha_i} \quad (7)$$

Let $B_{std}$ be the standard deviation of these terms. The second homogeneity term is introduced as:

$$P_{homogenity}(x) = e^{-\left(2 \cdot \frac{B_{std}(x)}{B_\sigma^+(x)}\right)^2} \quad (8)$$

This term is set to 0 if $B_\sigma^+(x) = 0$.

The third term is related to the fact that for tubular structures, the image gradient on the circumference should be pointing roughly to the center. In other words, the norm of the vector difference between gradient and its projection in the radial direction should be as small as possible. This way structures whose gradient projection in the radial direction is only a small portion of the total image gradient are eliminated. Mathematically, we define the average difference over the circumference as:

$$F_{rad}(x) = \frac{1}{N}\sum_{i=1}^{N} \|\nabla_\sigma I(x+\tau\sigma v_{a_i}) - b_i(x)v_{a_i}\| \quad (9)$$

And the third term is defined as:

$$P_{rad}(x) = e^{-\left(2\cdot\frac{F_{rad}(x)}{B_\sigma^+(x)}\right)^2} \quad (10)$$

This term is set to 0 if $B\_\sigma\hat{}+(x)$ is zero.

Finally, we combine the three terms in equation (6), (8) and (10):

$$M_\sigma(x) = B_\sigma^+(x) P_{rad}(x) P_{homogeneity}(x) \quad (11)$$

We are interested in detecting vessels with a range of radii, therefore we repeat the previous process for several radii and take the maximum scale response for each voxel:

$$M(x) = \max_\sigma(M_\sigma(x)) \quad (12)$$

Figure 7:
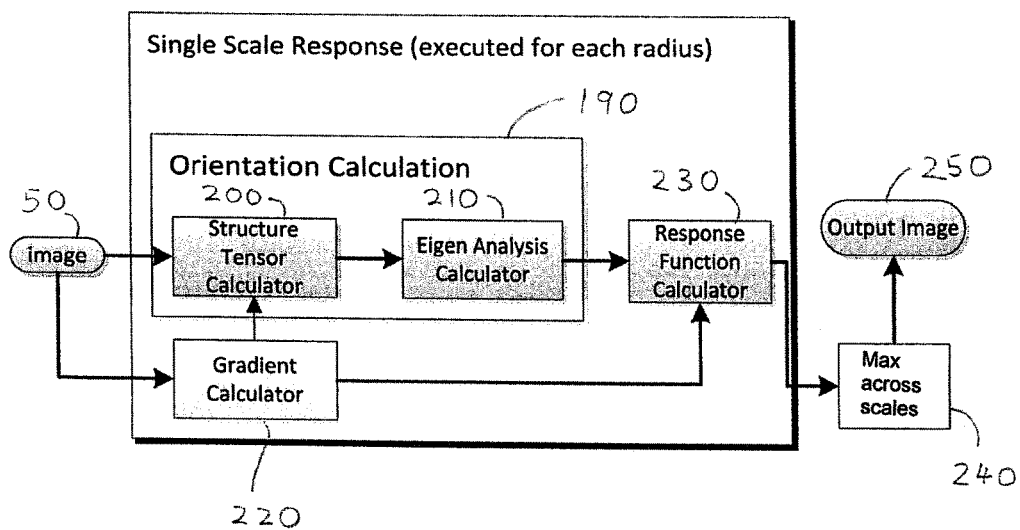
FIG. 7 is a block diagram outlining the algorithm for vessel enhancement.

FIG. 7 is a block diagram which outlines the vessel enhancement approach described above. Once the 3DUS image is obtained, an orientation calculation 190 is performed thereon, comprising a Structure Tensor calculation step 200 followed by an Eigen analysis calculation 210. Alternatively, an analysis of image gradient directions near the voxel may be performed (steps 220 and 190) to determine a direction vector which minimizes the average projection of the gradients near the vessel in order to find the vessel orientation. Next, a response function calculation (step 230) is performed. The foregoing process (including the structure tensor calculation and response function calculation) is repeated for several radii and the maximum scale normalized response (step 240) for each voxel is determined to derive an enhanced output image (step 250).

Metric Optimization.

The metric optimization will calculate a rigid body transformation from the fixed image to the moving image such that:

$$T(x_f) = Rx_f + o = x_m \quad (13)$$

where $x_f$ is the point coordinates in the fixed image, $x_m$ is the corresponding point coordinates in the moving image, R is a rotation matrix and o is the offset vector. The transform T can be parameterized with 6 parameters as follows: $[v_1, v_2, v_3]$—is a versor representing the rotation matrix R and $[o_x, o_y, o_z]$ represent the offset vector o. (A versor is basically a Quaternion whose direction part was normalized to magnitude 1, and therefore can be represented by 3 numbers, instead of 4; this proves advantageous for optimization purposes since one less variable is needed to be optimized).

A common practice is to search for a set of transform parameters which optimize a certain metric, such as NCC or MI, which is applied directly to the two images. In the present case, the relevant image content, which are the vessels, take up a relatively small portion of the image. If our preprocessing method is successful then voxels which don't belong to a vessel, which constitute the majority of the voxels in both images, will have a very low value compared to the voxels on the vessel. Thus, if low value voxels are ignored, the preprocessed images become sparse and we can use that property to use a "point set to image" rather than an "image to image" registration approach. In this process a set of point coordinates of voxels of interest are extracted from the fixed image (voxels of interest could be all of the voxels whose value is above 0 for example), and for each point coordinate, a relevant data attribute could be associated (e.g. the interpolated value of the image at that point). The point set can be registered to and image in a similar fashion to registering and image to another image. The major advantage of the point set to image approach over the image to image approach is speed, since a metric calculation is only needed for a subset of the voxels in the fixed image rather than for the whole image.

The first step is to threshold the preprocessed fixed image and set every voxel which has a low probability of being on a vessel to zero and every remaining voxel value to one (effectively making the image a binary). The criterion for zeroing voxels is any voxel whose value is less than 1% of the maximal value in the preprocessed fixed image. After that the image is cleaned using connected components analysis to remove isolated components whose size is 1 voxel or less, which are most probably attributed to noise. All the remaining voxels coordinates whose value is 1 are added to a point set P. Thus, all the points in P have high probabilities of being on or close to a vessel centerline.

The objective is to find a transformation which maximizes the average intensity in the preprocessed image which the points in P map to. A transform that maximizes the former is in fact mapping high probability fixed image voxels to high probability moving image voxels and therefore yield good image alignment.

We define the following mean squared difference ("MSD") metric:

$$MSD(T, P, M_m) = \frac{1}{\|P\|}\sum_{x \in P}(c - M_m(T(x)))^2 \quad (14)$$

where $M_m$ is the pre-processed moving image and c is a constant. This is a mean squared difference between the pre-processed moving image and the point set, if each point in the point set had value c associated with it. If we choose the value of the constant c such that it is greater than the maximum of $M_m$, then the difference in each term in (14), before the square operation, will be always positive. Thus, for each term, the higher the value of $M_m$, the lower value of the metric. On the other hand, terms in which a point in P maps to low intensity voxel in $M_m$ will increase the metric. Thus, a minimizer of the metric will achieve the objective of mapping the most high probability vessel voxels in the fixed image to high probability voxels in the moving image. It is empirically found that setting the value for c as c=100, works well for all tested images.

The MSD metric is minimized with respect to the parameterization of T using a regular step gradient descent optimization algorithm. The optimization starts from an initial guess of T, which is required to be sufficiently close to the solution. The optimization iteratively tries to improve the solution by taking steps in the parametric space along the direction of the negative gradient of the MSD metric. The process stops when a minima of the MSD metric is reached or the number of iterations is exceeded. The latter case means that the optimization was unable to find a solution.

To get a good solution, we need to look for the global minima—but with gradient descent, there is a risk of reaching a local minima, which could yield a bad result. To accommodate for this, the most common practice is a multi-scale optimization approach. In this approach, the image blurred with a Gaussian kernels with decreasing scale (variance). For the first image, which has the highest scale, the optimization is initialized with the input transform. For the rest of the images, the optimization is started from the final transform of the previous scale level. We used 3 scales with the following variances in millimeter units: 4.0, 2.0, and 1.0.

Finally, the metric optimization algorithm described above was implemented using the ITK tool kit which is a tool kit for medical image registration and segmentation. An in-depth description and discussion of the specific components used, such as the regular step gradient descent algorithm, is provided in the tool kit's documentation (available at (www.itk.org)), which is incorporated herein by reference.

Blending.

In the blending process the two images are combined in a seamless manner such that the transition from one image volume to the other image volume is smooth. This is achieved through the use of a distance transform based weighting of the voxel values. For calculating distance transform, a background mask is first calculated for both the fixed and moving images. The mask has 0 for foreground zone, which corresponds to the portion of the volume inside the field of view of the US scan, and 1 for the background volume. The value of distance transform is the Euclidean distance to the closest 1 voxel in the mask. The images are blended according to the following formula:

$$I(x, y, z) = \frac{D_1(x, y, z)}{D_1(x, y, z) + D_2(T(x, y, z))} I_1(x, y, z) + \frac{D_2(T(x, y, z))}{D_1(x, y, z) + D_2(T(x, y, z))} I_2(T(x, y, z)) \quad (15)$$

Where $I(x,y,z)$ is the blended image, $I_1(x,y,z)$ is the fixed image, $I_2(x,y,z)$ is the moving image, and T is the transform from the registration. $D_1(x,y,z)$, $D_2(x,y,z)$ are the distance transforms of the two images. (In the case where $D_1(x,y,z)+D_2(x,y,z)=0$, we set $I(x,y,z)=0$). As can be seen from the formula, the relative weighting of voxel values increases as it is farther from the edge of the foreground zone, meaning it is closer to the center of the image.

What is claimed is:

1. A computer-implemented method for combining two 3D ultrasound images of a body part containing at least one blood vessel, into a single 3D ultrasound image with a greater field of view, comprising:
   using at least one processing unit to receive a first 3D ultrasound image of said body part, a second 3D ultrasound image of said body part, and an initial transform, wherein the first ultrasound mage overlaps with the second ultrasound image in an overlapping region;
   using the at least one processing unit to perform a preprocessing vessel enhancement step on the first 3D ultrasound image in order to derive a first enhanced image;
   using the at least one processing unit to perform a preprocessing vessel enhancement step on the second 3D ultrasound image in order to derive a second, enhanced image;
   using the at least one processing unit to perform a registration step on the first enhanced image; the second enhanced image and the initial transform, in order to derive a refined transform;
   using the at least one processing unit to perform a blending step on the first and second enhanced images, using the refined transform, thereby obtaining an output image; and
   using the at least one processing unit to output the output image.

2. The computer-implemented method of claim 1, wherein each of the preprocessing vessel enhancement steps comprise:
   selecting at least one radius estimate for the at least one blood vessel and for each at least one radius estimate, performing a single scale response calculation using said at least one radius estimate, and
   determining a maximum scale normalized response from the single scale response calculations.

3. The computer-implemented method of claim 2, wherein the single scale response calculation comprises:
   performing an orientation calculation to determine the orientation of the at least one blood vessel, and performing a response function calculation.

4. The computer-implemented method of claim 3, wherein the orientation calculation comprises a structure tensor calculation and an Eigen analysis calculation.

5. The computer-implemented method of claim 1, wherein the registration step is a metric optimization step comprising:
   creating a set of points from the first enhanced image; and
   determining a refined transform between the set of points and the second enhanced image using the initial transform.

6. The computer-implemented method of claim 5, wherein the determining a refined transform between the set of points and the second enhanced image, is determined by calculating the transform which minimises the mean-square-difference metric between the set of points and the second enhanced image.

7. The computer-implemented method of claim 1, wherein the registration step additionally comprises:
   for each voxel of the first enhanced image, determining a probability value corresponding to the probability that the voxel corresponds to the at least one blood vessels;
   adding each voxel of the first enhanced image which has a high probability of corresponding to the at least one blood vessel to a set of points;
   and performing the registration step based upon the set of points and the second enhanced image in order to derive a refined transform.

8. The computer-implemented method of claim 7, wherein prior to performing the registration step based upon the set of points and the second enhanced image in order to derive a refined transform, isolated points are removed from the set of points.

9. The computer-implemented method of claim 7, wherein the derive a refined transform step is determined by calculating the transform which minimises the mean-square-difference metric between the set of points and the second enhanced image.

10. The computer-implemented method of claim 1, wherein the blending step comprises:
    application of a distance transform based weighting of each voxel in the overlapping region of the first and second enhanced images.

11. The computer-implemented method of claim 10, wherein the distance transform based weighting is calculated by:
- generating a binary mask for each voxel in the first and second enhanced images, wherein each voxel within the field of view of the first and second enhanced images is assigned a mask value of zero and wherein each voxel outside the field of view of the first and second enhanced images is assigned a mask value of one; and
- determining the value of the distance transform, which is determined by the Euclidean distance to the closest voxel having a mask value of one in the binary mask.

* * * * *